United States Patent [19]

Motegi et al.

[11] Patent Number: 5,113,000

[45] Date of Patent: May 12, 1992

[54] ORGANOSILICON COMPOUND AND ACRYL COMPOUND

[75] Inventors: Hisao Motegi; Takeshi Sunaga; Michio Zembayashi, all of Ohta, Japan

[73] Assignee: Toshiba Silicone Co., Ltd., Japan

[21] Appl. No.: 622,663

[22] Filed: Dec. 5, 1990

[30] Foreign Application Priority Data

| Dec. 13, 1989 | [JP] | Japan | 1-323390 |
| Dec. 13, 1989 | [JP] | Japan | 1-323391 |
| Dec. 18, 1989 | [JP] | Japan | 1-326156 |
| Dec. 22, 1989 | [JP] | Japan | 1-331040 |

[51] Int. Cl.⁵ .............................. C07F 7/08; C07F 7/10; C07F 7/12
[52] U.S. Cl. .............................. 556/413; 556/440; 549/215; 560/225
[58] Field of Search .............. 556/413, 440; 549/215; 560/225

[56] References Cited

U.S. PATENT DOCUMENTS

| 2,832,754 | 4/1958 | Jex et al. | 556/413 |
| 3,146,250 | 8/1964 | Speier | 556/413 |
| 3,673,233 | 6/1972 | Golltz et al. | 556/413 |
| 4,481,364 | 11/1984 | Chu et al. | 556/413 |
| 4,659,798 | 4/1987 | Pohl et al. | 556/413 X |

Primary Examiner—Arthur C. Prescott

[57] ABSTRACT

An organosilicon compound represented by the general formula:

$$X_2CHCH_2-\underset{\underset{Y_n}{|}}{Si}-R^1{}_{3-n}$$

where $R^1$ represents a substituted or non-substituted monovalent hydrocarbon group, X represents a chloromethyl group, (meth)acryloxymethyl group, glycidoxymethyl group or aminomethyl group, Y represents a hydrolyzable group or hydroxyl group, n represents a number of 1, 2 or 3. The compound is useful, for example, for the improvement of adhesion between the organic and inorganic materials.

6 Claims, No Drawings

ORGANOSILICON COMPOUND AND ACRYL COMPOUND

The present application claims the priority of Japanese Patent Applications Serial No. 1-323390 and No. 1-323391 both filed on Dec. 13, 1989, No. 1-326156 filed on December 18, 1989 and No. 1-331040 filed on Dec. 22, 1989.

FIELD OF THE INVENTION

The present invention concerns a novel organosilicon compound and an intermediate product thereof which are useful, for example, for the improvement of adhesion between organic and inorganic materials.

BACKGROUND OF THE INVENTION

Organosilicon compounds which have been used to improve the adhesion of organic inorganic composite materials include known various silane coupling agents such as γ-chloropropyl trimethoxysilane, γ-aminopropyl trimethoxysilane, γ-glycidoxypropyl trimethoxysilane, γ-methacryoxypropyl trimethoxysilane and γ-mercaptopropyl trimethoxysilane. However, since these silanes have only one functional carbon group, they cannot be used as a crosslinking agent between organic polymers. There exists a need for organosilicon compounds having two functional carbon groups for use in the improvement of adhesion between organic and inorganic materials.

SUMMARY OF THE INVENTION

The present invention is directed to an organosilicon compound having two functional carbon groups and an intermediate product thereof which are useful for the improvement of the adhesion of organic inorganic composite materials typically represented by sealing agents for semiconductor.

The organosilicon compound of the present invention is represented by the following general formula (1)

in which $R^1$ represents a substituted or non-substituted monovalent hydrocarbon group, X represents $ClCH_2$-,

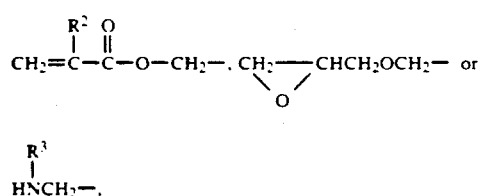

Y represents a hydrolyzable group or hydroxyl group, n represents a number of 1, 2 or 3, $R^2$ represents a hydrogen atom or a methyl group and $R^3$ represents a hydrogen atom or a substituted or non-substituted monovalent hydrocarbon group.

An acrylic compound useful as an intermediate product in the present invention is represented by the following general formula (2):

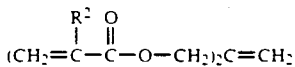

in which $R^2$ has the same meanings as described above.

DETAILED DESCRIPTION OF THE PRESENT INVENTION

In compound (1) of the present invention, $R^1$ is a substituted or non-substituted monovalent hydrocarbon group. Examples of groups represented by $R^1$ include alkyl groups such as methyl, ethyl, propyl, butyl, pentyl, hexyl, heptyl, octyl, nonyl, decyl and dodecyl groups; cycloalkyl groups such as cyclopentyl and cyclohexyl groups; aralkyl groups such as 2-phenylethyl and 2-phenylpropyl group; aryl groups such as phenyl and tolyl groups; alkenyl groups such as vinyl and allyl groups; as well as hydrocarbon groups substituted with such groups as halogen atoms, amino groups or cyano groups. Examples of suitable substituted hydrocarbon groups include chloromethyl groups, chlorophenyl groups, 3,3,3-trifluoropropyl groups, aminoethyl groups and cyanoethyl groups, in which hydrogen atoms bonded to carbon atoms of the monovalent hydrocarbon group as described above are partially substituted. Among them, saturated hydrocarbon groups with 1 to 4 carbon atoms, particularly methyl groups, are particularly preferred in view of the availability of starting materials and easy synthesis.

In compound (1) of the present invention, Y is a hydrolyzable group or hydroxy group. As the hydrolyzable group, there can be mentioned, for example, alkoxy groups such as methoxy, ethyoxy, n-propoxy, i-propoxy, methoxyethoxy, n-butoxy, sec-butoxy, i-butoxy, t-butoxy, cyclohexyloxy and phenoxy; alkenyloxy groups such as isopropenyloxy group; ketoxime groups such as diethylketoxime group; acyloxy groups such as acetoxy group; amino groups such as diethylamino group; aminoxy groups such as diethylaminoxy group; and halogen atoms such as chlorine. Among them, alkoxy groups, chlorine atoms and hydroxy groups are preferred and, particularly, the methoxy group is preferred in view of easy synthesis, stability and moderate reactivity.

In compound (1) of the present invention, n represents the number for the hydrolyzable group Y and is 1, 2 or 3. Preferably, n is 3, in the case of using compound (1) of the present invention for the improvement of adhesion between the organic and inorganic materials.

In compound (1) of the present invention, the functional carbon group X is $ClCH_2$-,

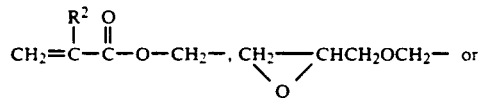

$R^2$ is a hydrogen atom or methyl group. Specific examples of

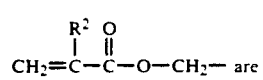 are

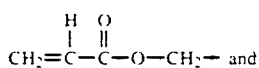

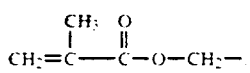

$R^3$ is a hydrogen atom or a substituted or non-substituted monovalent hydrocarbon group. Examples of groups represented by $R^3$ include hydrogen atoms; alkyl groups such as methyl, ethyl, propyl, butyl, pentyl, hexyl, heptyl, octyl, nonyl, decyl and dodecyl groups; cycloalkyl groups such as cyclopentyl and cyclohexyl groups; aralkyl groups such as 2-phenylethyl and 2-phenylpropyl groups; aryl groups such as phenyl and tolyl groups; alkenyl groups such as vinyl and allyl groups; and substituted hydrocarbon groups such as chloromethyl group, chlorophenyl group, 3,3,3-trifluoropropyl group, aminoethyl group and cyanoethyl group in which hydrogen atoms bonded to the carbon atoms of the monovalent hydrocarbon group as described above are partially substituted with halogen atoms, amino groups or cyano groups. Among them, hydrogen atoms and butyl groups are preferred in view of the availability for the starting materials and easy synthesis.

An example of a method for making compound (1) is to conduct an addition reaction between a compound having two functional carbon groups represented by the general formula (3):

$$X_2C=CH_2 \quad (3)$$

in which X has the same meanings as described above, and a silane compound represented by the general formula (4):

(4)

in which Y and n have the same meanings as described above. The chemical reaction scheme is shown in the following formula (I):

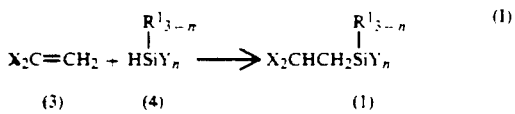

in which $R^1$, Y and n have the same meanings as described above.

In compound (I) of the present invention, $X_2C=CH_2$ (3) used as the starting material can include, for example, the followings:

$(ClCH_2)_2C=CH_2$ (5)

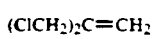

(6)

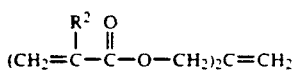

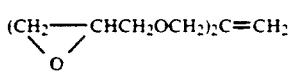

(7)

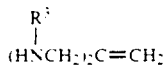

in which $R^2$ and $R^3$ have the same meanings as described above.

Methods for preparing the compounds of formulae are discussed below.

$(ClCH_2)_2C=CH_2$ (5)

3-chloro-2-(chloromethyl)propene represented by formula (5) is a known material, which can be obtained, for example, by chlorinating 3-chloro-3-methylpropene with sulfuryl chloride (European Patent Specification No. 159508) or by reacting methylene cyclopropane with chlorine gas (R.Koester, S. Arora, P. Binger: Justus Liebigs Ann. Chem., 10, 1619 (1973)).

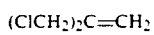

(6)

2-methylene-1,3-di(meth)acryloxypropane (6), another compound of the present invention useful as thestarting material for the preparation of compound (1) in accordance with the present invention, is a novel compound and can be synthesized by the following process.

In this process, 3-chloro-2-(chloromethyl)-propene (5) and acrylic acid (9) are made to undergo dehydrochlorination in the presence of a strong base, for example, 1,8-diazabicyclo-(5,4,0)-7-undecene (hereinafter simply referred to as DBU). This is shown by the chemical reaction scheme (II):

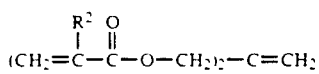

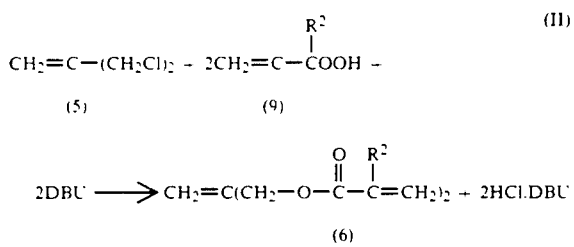

in which $R^2$ has the same meanings as described above.

Compound (9) is acrylic acid or methacrylic acid which are commercially available products.

The reaction of the reaction scheme (II) can be conducted by adding, to the compound (5) a mixed solution of compound (9) in an equi-molar amount and DBU at a liquid temperature of 50° to 60° C. and reacting them in an aromatic hydrocarbon solvent. As the aromatic hydrocarbon solvent used in the reaction, there can be mentioned, benzene, toluene or xylene and, among all, toluene is preferably used in view of operation and safety.

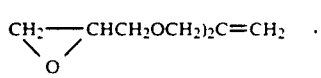

(7)

2-methylene-1,3-diglycidoxypropane represented by formula (7) is prepared, for example, as described below.

At first, 2-methylne-1,3-propanediol (10) and epichlorohydrine (11) are addition reacted in the presence of an acid catalyst to form a chlorohydrine derivative 12), which is then made to undergo dehydrochlorination with a basic hydroxide, for example, sodium hydroxide, to synthesize 2-methylene-1,3-diglycidoxypropane (7). This can be represented by the chemical reaction scheme as below:

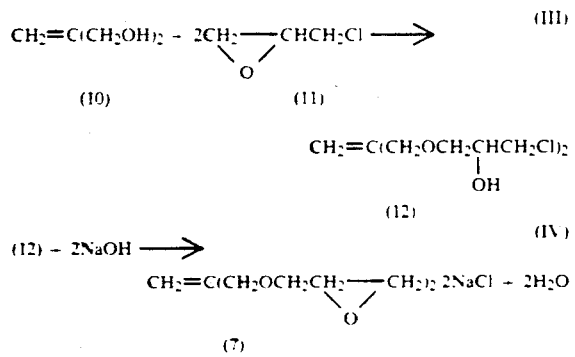

The compound (10) can be prepared by a method wherein 5-norbornen-2-ylidene dimethanol is reacted in a retro-Diels Alder reaction (E. J. Corey, J. W. Suggs; Tetrahedron Lett., 44, 3775–3778 (1975)), or in a method wherein 2-methylene-1,3-propanediol diacetate is synthesized through acetic acid esterification of 3-chloro-2-(chloromethyl)propane, which is then made to undergo an ester exchanging reaction with methanol (Y. Ducharme, S. Latour, J. D. Wuest; Organometallics, 3, 208–211 (1984)).

The amine compound represented by (8) above can be prepared as described below. The amine compound wherein $R^3$ is a hydrogen atom is 1,3-diaminomethylenepropane, which can be synthesized from 3-chloro-2-(chloromethyl)propene (5) by Gabriel's method (East German Patent Specification No. 113746 (1975)) which is incorporated by reference herein. Further, the amine compound (8) in which R3 is a substituted or non-substituted monovalent hydrocarbon can be synthesized, for example, by a dehydrochlorination reaction between 3-chloro-2-(chloromethyl)propene (5) and a primary amine (13) as shown by the scheme (V)

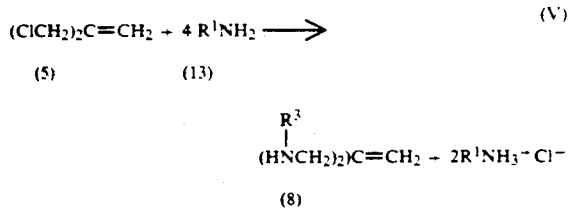

where $R^3$ has the same meanings as described above.

The silane compound (4) used as the starting material in the preparation of compound (1) in accordance with the present invention is a known material. As the silane compound (4), there can be mentioned, for example, monohydrogen halogenosilane such as trichlorosilane, tribromosilane, methyldichlorosilane, dimethylchlorosilane, ethyldichlorosilane, diethylchlorosilane and phenyldichlorosilane; monohydrogen alkoxysilane such as trimethoxysilane, triethoxysilane, methyldimethoxysilane and dimethylethoxysilane; and monohydrogen silanol such as diethylsilanol, diphenylsilanol and methylphenylsilane. In addition, there can be also mentioned those monohydrogen silanes having alkenyloxy groups, ketoxime groups, acyloxy groups, amino groups or aminoxy groups. Among them, monohydrogen halogenosilane, monohydrogen alkoxysilane and monohydrogen silanol are preferred, with trimethoxysilane being particularly preferred in view of the availability for the starting materials, easy synthesis and reactivity.

In the addition reaction shown in scheme (I), there is no particular restriction on the ratio of compound (3) to silane compound (4). However, since one mole of the hydrosilyl group of the silane compound (4) reacts with one mole of the vinylidene group in the compound (3), use of them each in an equi-molar amount for the reaction is preferred form an economical point of view.

As the catalyst for the addition reaction of scheme (I), there can be used complex compounds of metals belonging to the group VIII of the periodical table and a platinum compound prepared by dissolving chloroplatinic acid into an alcohol or a carbonyl compound or a complex compound of various olefins with platinum or rhodium. Although there is no particular restriction on the amount of the complex compound used, it is preferably within a range from 10 ppm to 2,000 ppm as the platinum atom based on the amount of compound (3) used. If it is less than 10 ppm, the reaction rate is slow and no satisfactory yield can be obtained in a short period of time. Further, if it is more than 2,000 ppm, no particular effect can be obtained by the addition.

For the addition reaction of scheme (I), a method wherein the compound (3) and the catalyst are mixed, heated to a predetermined temperature, followed by dropping of the silane compound (4) is preferred in view of the reaction control.

The reaction temperature for the addition reaction is, usually, from 10° to 250° C. and, preferably, from 40° to 150° C. The reaction time can be varied within a range from 0.1 to 50 hours depending on the amount of the catalyst used, reaction temperature and the molar ratio of the starting materials. The reaction can be conducted either under a normal pressure or at high pressure.

In the addition reaction of scheme (I), use of the organic solvent is not essential but, when it is used, it is possible to use aliphatic hydrocarbons such as hexane and heptane; cycloaliphatic hydrocarbon such as cyclohexane; ethers such as diethyl ether; aromatic hydrocarbons such as benzene, toulene and xylene and halogenated hydrocarbons such as 1,2-dichloroethane. Although there is no particular restriction on the amount of organic solvent used, it is preferably used within a range from 10 to 500% by weight based on the total weight of the reaction materials.

Another method for producing the compound (1) according to the present invention involves carrying out a substitution reaction between the chlorosilane compound (14) and a compound having active hydrogen and represented by the general formula (15). The process is shown by means of the reaction scheme (VI).

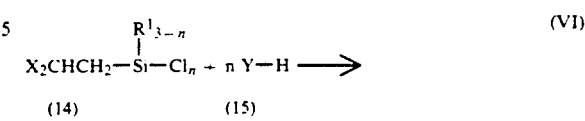

-continued

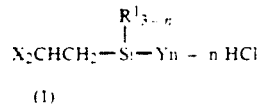

(1)

where $R^1$, Y and n have the same meanings as described above.

Examples of compounds represented by formula (15), include alcohol such as methanol, ethanol, n-propanol, i-propanol, methoxyethanol, n-butanol, secbutanol, i-butanol, t-butanol and cyclohexanol; as well as phenol. Among them, methanol and ethanol are preferred.

In the substitution of reaction scheme (VI), it is desirable to use a hydrogen chloride catcher corresponding to the theoretical equivalent amount for proceeding the reaction smoothly. A tertiary amine such as pyridine, triethylamine or tributylamine is preferred as the hydrogen chloride catcher.

In the substitution reaction of scheme (VI), use of the organic solvent is not essential but, if it is used, the organic solvents previously discussed herein can be used.

In a preferred embodiment of the substitution reaction of scheme (VI) in view of the reaction control, the chlorosilane compound (14) and, if required, an organic solvent are charged to the reaction vessel, and then a mixture of the compound (15) having an active hydrogen and the hydrogen chloride catcher each in a theoretical equivalent amount is dropped to them to react at a temperature from $-10°$ C. to $50°$ C.

Compound (1) can be isolated and purified from the thus obtained reaction mixture by any customary method employed in the field of organic synthesis chemistry. For example, target material can be isolated by distillation under reduced pressure.

Because the compound of the present invention has two substituting groups which react or interact with an organic matrix resin, it is effective for the improvement of the adhesion and the reliability of organic - inorganic composite materials such as sealers for semiconductors. Furthermore, in the organic-inorganic complex material, there can be also expected improvement in mechanical properties, the electrical properties, water proofness and moisture proofness, workability, and cost reduction due to the blending of the inorganic filler at high blending ratio. Further, an intermediate product, 2-methylene-1,3-di(meth)acryloxy propane (2) as a novel compound is one of the starting materials useful for the production of the above-mentioned compound.

The present invention will now be described more specifically referring to examples. However, it should be understood that the present invention is not restricted only to the following examples. In the Examples, all parts are by weight.

EXAMPLE 1

Synthesis of 2-chloromethyl-3-(chloropropyl) trichlorosilane 2.0 parts of a solution prepared by dissolving 0.5 parts of chloroplatinic acid into 25 parts of isopropanol and 125 parts of 3-chloro-2-chloromethyl propene were charged into a flask of 1 liter inner volume, equipped with a stirrer, a thermometer, a dropping funnel, a refluxing condenser and an oil bath. Stirring was started and the solution was heated to a temperature of 70° C.

135.5 parts of trichlorosilane were dropped form the dropping funnel onto the solution for one hour under appropriate cooling such that the liquid temperature was kept at 80°~90° C. After the dropping was complete, the solution was stirred with heating at a temperature of 80° C. for 2 hours. It was confirmed by gas chromatographic analysis that the starting material was substantially eliminated.

After standing to cool, when fractions boiling at 115°~117° C./16 Torr were collected by distillation under a reduced pressure, 208.4 parts (80.0% yield) of 2-chloromethyl-3-chloropropyl trichlorosilane were obtained as a colorless transparent liquid.

The results of gas chromatographic analysis elemental analysis, IR absorption spectral analysis and $^1$H NMR analysis were as shown below and it was confirmed that the product had the molecular structure of the following formula:

| | a | b | c |
|---|---|---|---|
| | $Cl_3Si-CH_2CH(CH_2Cl)_2$ | | |

| Gas chromatographic analysis purity 95.3% Elemental analysis: | |
|---|---|
| Measured value. | Si: 10.75%, C: 18.47%, H: 2.69%, Cl: 68.09% |
| Calculated value | Si: 10.78%, C: 18.45%, H: 2.71%, Cl: 68.06% |

| IR absorption spectral analysis (liquid film method) | |
|---|---|
| Number of wave (cm$^{-1}$) | Belonging to |
| 2940 | C—H |
| 830 | C—Cl |

EXAMPLE 2

Synthesis of 2-chloromethyl-3-(chloropropyl) trimethoxysilane

| $^1$NMR analysis (90 MHz in CDCl$_3$) | | | |
|---|---|---|---|
| Position | Chemical shift δ (ppm) | Integral intensity | Multiplicity |
| a | 0.9~1.2 | 2H | d |
| b | 2.1~2.5 | 1H | m |
| c | 3.6~3.8 | 4H | d |

207.0 parts of 2-chloromethyl-3-chloropropyl trichlorosilane and 700 parts of n-hexane were charged into a flask of 2 liter inner volume, equipped with a stirrer, a thermometer, a dropping funnel, a refluxing condenser and an ice bath. Stirring was started and the solution was cooled to a temperature of 0° C.

A mixed solution of 76.8 parts of methanol and 189.6 parts of pyridine was dropped rom the dropping funnel onto the first solution for one hour such that the liquid temperature was kept at 0°~20° C. After the dropping was complete, the solution was stirred at a room temperature for 2 hours and it was confirmed by gas chromatographic analysis that 2-chloromethyl-3-chloropropyl trichlorosilane was eliminated.

After filtering the pyridine hydrogen chloride salt by-product, when fractions boiling at 127°~129° C./17 Torr were collected by distillation under a reduced pressure, 169.9 parts of 2-chloromethyl-3-chloropropyl tri-methoxysilane were obtained as a colorless transparent liquid. The yield was 86.0% based on 2-chloromethyl-3-chloropropyl trichlorosilane.

The results for the gas chromatographic analysis, elemental analysis, IR absorption spectral analysis, $^1$H NMR analysis and mass spectral analysis were as shown below and it was confirmed that the product had the molecular structure of the following formula:

| a b c d |
|---|
| (CH$_3$O)$_3$Si—CH$_2$CH(CH$_2$Cl)$_2$ |

Gas chromatographic analysis: purity 97.3%
Elemental analysis:

| | |
|---|---|
| Measured value: | Si: 11.39%, C: 34.00%, H: 6.50%, O: 19.43%, Cl: 28.68% |
| Calculated value | Si: 11.36%, C: 34.01%, H: 6.53%, O: 19.42%, Cl: 28.68% |

IR absorption spectral analysis (liquid film method)

| Number of wave (cm$^{-1}$) | Belonging to |
|---|---|
| 2940 | C—H |
| 1100–1080 | Si—OCH$_3$ |
| 830 | C—Cl |

$^1$NMR analysis (90 MHz in CDCl$_3$)

| Position | Chemical shift δ (ppm) | Integral intensity | Multiplicity |
|---|---|---|---|
| a | 3.5 | 9H | s |
| b | 0.7–0.9 | 2H | d |
| c | 2.1–2.5 | 1H | m |
| d | 3.6–3.8 | 4H | d |

Mass spectral analysis (m/e) 246 (M$^+$)

EXAMPLE 3

Synthesis of 2-chloromethyl-3-chloropropyl methyldichlorosilane

Reaction was proceeded according to the same procedures followed in Example 1 except that 115.0 parts of methyldichlorosilane were used as the chlorosilane.

After standing to cool, when fractions boiling 111°–116° C./16 Torr were collected by distillation under a reduced pressure, 168.0 parts (70% yield) of 2-chloromethyl-3-chloropropyl methyldichlorosilane were obtained as a colorless transparent liquid.

The results for the gas chromatographic analysis, elemental analysis, IR absorption spectral analysis and $^1$H NMR analysis were as shown below and it was confirmed that the product had the molecular structure of the following formula:

| a b c d |
|---|
| CH$_3$ |
| \| |
| Cl$_2$Si—CH$_2$CH(CH$_2$Cl)$_2$ |

Gas chromatographic analysis purity 95.0%
Elemental analysis:

| | |
|---|---|
| Measured value: | Si: 11.73%, C: 25.02%, H: 4.18%, Cl: 59.07% |
| Calculated value | Si: 11.70%, C: 25.02%, H: 4.20%, Cl: 59.08% |

IR absorption spectral analysis (liquid film method)

| Number of wave (cm$^{-1}$) | Belonging to |
|---|---|
| 2940 | C—H |
| 1240 | Si—CH$_3$ |
| 830 | C—Cl |

$^1$NMR analysis (90 MHz in CDCl$_3$)

| Position | Chemical shift δ (ppm) | Integral intensity | Multiplicity |
|---|---|---|---|
| a | 0.5 | 3H | s |
| b | 0.9–1.2 | 2H | d |
| c | 2.1–2.5 | 1H | m |

-continued

| a b c d |
|---|
| CH$_3$ |
| \| |
| Cl$_2$Si—CH$_2$CH(CH$_2$Cl)$_2$ |

| d | 3.6–3.8 | 4H | d |
|---|---|---|---|

EXAMPLE 4

Synthesis of 2-chloromethyl-3-chloropropyl methyldimethoxysilane 167.0 parts of 2-chloromethyl-3-chloropropyl methyldichlorosilane and 600 parts of n-hexane were charged into a flask of 2 liter inner volume, equipped with a stirrer, a thermometer, a dropping funnel, a refluxing condenser and an ice bath. Stirring was started and the solution was cooled to a temperature of 0° C.

A mixed solution of 44.8 parts of methanol and 110.6 parts of pyridine was dripped from the dropping funnel onto the first solution for 0.5 hour such that the liquid temperature was kept at 0°–20° C. After the dropping was complete, the solution was stirred at a room temperature for 2 hours and it was confined by gas chromatographic analysis that the 2-chlroomethyl-3-chlroopropyl methyldichlorosilane was eliminated.

After filtering the pyridine hydrogen chloride salt by-product, when fractions boiling at 121°–122° C./23 Torr were collected by distillation under a reduced pressure, 143.9 parts of 2-chloromethyl-3-chloropropyl methyldimethoxysilane were obtained as a colorless transparent liquid. The yield was 89.0% based on 2-chloromethyl-3-chloropropyl methyldichlorosilane.

The results for the gas chromatographic analysis, elemental analysis, IR absorption spectral analysis, $^1$H NMR analysis and mass spectral analysis were as shown below and it was confirmed that the product had the molecular structure of the following formula:

| a b c d e |
|---|
| CH$_3$ |
| \| |
| (CH$_3$O)$_2$Si—CH$_2$CH(CH$_2$Cl)$_2$ |

Gas chromatographic analysis: purity 97.7%
Elemental analysis:

| | |
|---|---|
| Measured value: | Si: 12.17%, C: 36.36%, H: 6.96%, O: 13.85% Cl: 30.66% |
| Calculated value | Si: 12.15%, C: 36.36%, H: 6.98%, O: 13.84% Cl: 30.67% |

IR absorption spectral analysis (liquid film method)

| Number of wave (cm$^{-1}$) | Belonging to |
|---|---|
| 2940 | C—H |
| 1240 | Si—CH$_3$ |
| 1100–1080 | Si—OCH$_3$ |
| 830 | C—Cl |

$^1$NMR analysis (90 MHz in CDCl$_3$)

| Position | Chemical shift δ (ppm) | Integral intensity | Multiplicity |
|---|---|---|---|
| a | 3.5 | 6H | s |
| b | 0.3 | 3H | s |
| c | 0.7–0.9 | 2H | d |
| d | 2.1–2.5 | 1H | m |
| e | 3.6–3.8 | 4H | d |

Mass spectral analysis (m/e) 231 (M$^+$)

EXAMPLE 5

Synthesis of 2-methylene-2,3-dimethacryloxy propane 37.5 parts of 3-chloro-2-chloromethylpropene and 100 parts of toluene were charged into a flask of 500 ml inner volume equipped with a stirrer, a thermometer, a dropping funnel, a refluxing condenser and an oil bath. Stirring was started and the solution was heated at a liquid temperature of 50° C.

Then, a mixed solution previously prepared by dissolving 51.6 parts of methacrylic acid and 91.0 parts of DBU in 100 g of toluene was dropped onto the first solution for 2 hours under appropriate cooling through the dropping funnel such that the liquid temperature was kept at 50°~60° C. After dropping was complete, the resultant solution was heated under stirring for one hour at a liquid temperature of 60° C. and it was confirmed from the gas chromatographic analysis that 3-chloro-2-chloromethylpropene was eliminated and its ester derivative 2-methylene-1,3-dimethacryloxy-propane was formed.

Then, after cooling to a room temperature, DBU hydrogen chloride salt was separated by filtration and the filtrate was further washed twice each time with 100 ml of a saturated aqueous solution of sodium chloride and then dried with anhydrous sodium sulfate.

After drying, when fractions boiling at 98°~100° C./2 Torr were collected by distillation under a reduced pressure, 53.8 parts (yield 80%) of 2-methylene-1,3-dimethacyloxy propane were obtained as a colorless transparent liquid.

The results for the gas chromatographic analysis, elemental analysis, IR absorption spectral analysis, $^1$H NMR analysis and mass spectral analysis were as shown below and it was confirmed that the product had the molecular structure of the following formula:

$$\overset{a}{CH_2}=C(\overset{b}{CH_2}-O\overset{c}{C}O-\overset{d}{C}=\overset{e}{C}-H)_2 \quad | \quad \overset{}{CH_3} \; H$$

| Gas chromatographic analysis: purity 97.2% |  |
| --- | --- |
| Elemental analysis | |
| Measured value | C: 64.26%, H: 7.18%, O: 28.56% |
| Calculated value | C: 64.27%, H: 7.19%, O: 28.54% |

| IR absorption spectral analysis (liquid film method) | |
| --- | --- |
| Number of wave (cm$^{-1}$) | Belonging to |
| 2940 | C—H |
| 1715 | C=O |
| 1635 | C=C |

| $^1$NMR analysis (90 MHz in CDCl$_3$) | | | |
| --- | --- | --- | --- |
| Position | Chemical shift δ (ppm) | Integral intensity | Multiplicity |
| a | 5.3 | 2H | s |
| b | 4.75 | 4H | s |
| c | 2.0 | 6H | s |
| d | 5.6 | 2H | s |
| e | 6.15 | 2H | s |

Mass spectral analysis (m/e): 224 (M$^+$ peak)

EXAMPLE 6

Synthesis of 2-methacryloxymethyl-3-methacryloxypropyl trimethoxysilane 0.6 parts of a solution prepared by dissolving 0.5 parts of chloroplatinic acid in 25 parts of isopropanol, 224 parts of 2-methylene-1,3-dimethacryloxypropane synthesized in Example 5 and 0.5 parts of 2,5-di-t-butyl hydroquinone as a polymerization inhibitor were charged into a flask of 1 liter inner volume, equipped with a stirrer, a thermometer, a dropping funnel, a refluxing condenser and oil bath. Stirring was started and the mixture was heated at a liquid temperature of 50° C.

122 parts of trimethyoxysilane were dropped from the dropping funnel onto the solution for 2 hours with appropriate cooling such that the liquid temperature was kept at 50°~60° C. After dripping was complete, the mixture was heated under stirring for one hour at a liquid temperature of 60° C. and it was confirmed from the gas chromatographic analysis that the starting material was eliminated substantially.

Then, after allowing the mixture to cool to room temperature, 0.5 part of p-benzoquinone dioxime was added as a polymerization inhibitor during distillation and when fractions boiling at 150°~152° C./0.5 Torr were collected by distillation under a reduced pressure, 291 parts (84.0% yield) of 2-methacryloxymethyl-3-methacryloxypropyl trimethoxysilane were obtained as a pale yellow transparent liquid.

The results for the gas chromatographic analysis, elemental analysis, IR absorption spectral analysis, $^1$H NMR analysis and mass spectral analysis were as shown below and it was confirmed that the product had the molecular structure of the following formula:

$$(\overset{a}{CH_3O})_3Si-\overset{b}{CH_2}\overset{c}{C}H\overset{d}{CH_2}-O\overset{e}{C}-\overset{f}{C}=\overset{g}{C}-H)_2 \quad | \quad \overset{}{CH_3}\; H \quad | \quad O$$

| Gas chromatographic analysis: purity 95.0% | |
| --- | --- |
| Elemental analysis | |
| Measured value: | Si: 8.13%, C: 51.90%, H: 7.54% |
|  | O: 32.43% |
| Calculated value | Si: 8.11%, C: 52.00%, H: 7.56%, O: 32.33% |

| IR absorption spectral analysis (liquid film method) | |
| --- | --- |
| Number of wave (cm$^{-1}$) | Belonging to |
| 2940 | C—H |
| 1715 | C=O |
| 1100~1080 | Si—OCH$_3$ |

| $^1$NMR analysis (90 MHz in CDCl$_3$) | | | |
| --- | --- | --- | --- |
| Position | Chemical shift δ (ppm) | Integral intensity | Multiplicity |
| a | 3.5 | 9H | s |
| b | 0.4~0.6 | 2H | d |
| c | 1.8~2.2 | 1H | m |
| d | 3.9~4.1 | 4H | d |
| e | 2.0 | 6H | s |
| f | 5.6 | 2H | s |
| g | 6.2 | 2H | s |

Mass spectral analysis (m/e): 346 (M$^+$)

EXAMPLE 7

Synthesis of 2-glycidoxymethyl-3-qlycidoxy propyl trimethoxysilane 0.6 parts of a solution prepared by dissolving 0.5 parts of chloroplatinic acid into 25 parts of isopropanol and 200 parts of 2-methylene-1,3-diglycidoxypropane were charged into a flask of 1 liter inner volume, equipped with a stirrer, a thermometer, a dropping funnel, a refluxing condenser and an oil bath. Stirring was started and the mixture was heated at a liquid temperature of 70° C.

122 parts of trimethoxysilane were dropped from the dropping funnel for one hour under appropriate cooling such that the liquid temperature was kept at 80°~90° C. After dropping was complete, the mixture was heated under stirring for 2 hours at a liquid temperature of 90° C. and it was confirmed from the gas chromatographic analysis that the peak of the starting material was eliminated substantially.

Then, after standing to cool to a room temperature, when fractions boiling at 139°~141° C./0.5 Torr were collected by distillation under a reduced pressure, 273.7 parts (85.0% yield) of 2-glycidoxymethyl-3-glycidoxypropyl trimethoxysilane were obtained as a colorless transparent liquid.

The results for the gas chromatographic analysis, elemental analysis, IR absorption spectral analysis, $^1$H NMR analysis and mass spectral analysis were as shown below and it was confirmed that the product had the molecular structure of the following formula:

| a b c d e f g |
|---|
| (CH$_3$O)$_3$SiCH$_2$CH(CH$_2$OCH$_2$CH——CH$_2$)$_2$ |
| \\ / |
| O |

| Gas chromatographic analysis: purity 98% |  |
|---|---|
| Elemental analysis: | |
| Measured value: | Si: 8.72%, C: 48.40%, H: 8.15% |
|  | O: 34.73% |
| Calculated value | Si: 8.71%, C: 48.42%, H: |
|  | 8.13%, O: 34.74% |

| IR absorption spectral analysis (liquid film method) | |
|---|---|
| Number of wave (cm$^{-1}$) | Belonging to |
| 2950 | C—H |
| 1120~1060 | C—O—C |
| 1100~1080 | Si—OCH$_3$ |

| $^1$NMR analysis (90 MHz in CDCl$_3$) | | | |
|---|---|---|---|
| Position | Chemical shift δ (ppm) | Integral intensity | Multiplicity |
| a | 3.5 | 9H | s |
| b | 0.4~0.6 | 2H | d |
| c | 1.8~2.2 | 1H | m |
| d | 3.3~3.5 | 4H | d |
| e | 3.2~3.7 | 4H | m |
| f | 2.9~3.2 | 2H | m |
| g | 2.5~2.8 | 4H | d |

Mass spectral analysis (m/e): 322 (M$^+$)

EXAMPLE 8

Synthesis of 2-aminomethyl-3-aminopropyl trimethoxysilane 86 parts of 1,3-diamino-2-methylene propane and 0.02 parts (as plantinum atom) of a platinum complex containing 1,3,5,7-tetravinyl-1,3,5,7-tetramethylcyclotetrasiloxane as a ligand were charged into a flask of 500 ml inner volume, equipped with a stirrer, a thermometer, a dropping funnel, a refluxing condenser and an oil bath. Stirring was started and the mixture was heated at a liquid temperature of 70° C.

122 parts of trimethoxysilane were dropped from the dropping funnel onto the solution for 2 hours with heating such that liquid temperature was kept at 70°~90° C. After dropping was complete, the mixture was heated under stirring for 5 hours at a liquid temperature of 90° C. and it was confirmed from the gas chromatographic analysis that the peak of the starting material were eliminated substantially.

Then, after standing to cool to a room temperature, when fractions boiling at 120°~122° C./2 Torr were collected by distillation under a reduced pressure, 168.5 parts (81.0% yield) of 2-aminomethyl-3-aminopropyl trimethoxysilane was obtained as a colorless transparent liquid.

The results for the gas chromatographic analysis, elemental analysis, IR absorption spectral analysis, $^1$H NMR analysis and mass spectral analysis were as shown below and it was confirmed that the product had the molecular structure of the following formula:

| a b c d e |
|---|
| (CH$_3$O)$_3$SiCH$_2$CH(CH$_2$NH$_2$)$_2$ |

| Gas chromatographic analysis: purity 94.9% | |
|---|---|
| Elemental analysis: | |
| Measured value: | Si: 13.50%, C: 40.34%, H: |
|  | 9.67% O: 23.06% N: 13.43% |
| Calculated value | Si: 13.48%, C: 40.35%, H: |
|  | 9.68%, O: 23.04% N: 13.45 |

| IR spectral analysis (liquid film method) | |
|---|---|
| Number of wave (cm$^{-1}$) | Belonging to |
| 3360 | N—H |
| 3270 | N—H |
| 2900~2750 | C—H |
| 1100~1080 | Si—OCH$_3$ |

| $^1$NMR analysis (90 MHz in CDCl$_3$) | | | |
|---|---|---|---|
| Position | Chemical shift δ (ppm) | Integral intensity | Multiplicity |
| a | 3.5 | 9H | s |
| b | 0.35~0.5 | 2H | d |
| c | 1.3~1.6 | 1H | m |
| d | 2.5~2.7 | 4H | d |
| e | 1.0 | 4H | s |

Mass spectral analysis (m/e): 208 (M$^+$)

REFERENCE EXAMPLE 1

Synthesis of 1,3-bis(N-(n-butyl)amino)-2-methylene propane 730 parts of n-butylamine were charged into flask of 2 liter inner volume, equipped with a stirrer, a thermometer, a dropping funnel, a refluxing condenser and an oil bath, and stirring was started. Then, 250 parts of 2-chloromethyl-3-chloropropene were dropped onto the solution from the dropping funnel for one hour while keeping the liquid temperature at 20°~50° C. After dropping was over, the mixture was stirred under heating for 2 hours at a liquid temperature of 60° C. and it was confirmed by the gas chromatographic analysis that peaks for 2-chloromethyl-3-chloropropene were eliminated.

After standing to cool to a room temperature, ammonium salt by-product was removed by filtration and when fractions boiling at 160°~162° C./90 Torr were collected by distillation under a reduced pressure, 238 parts of 1,3-bis(N-(n-butyl)amino)-2-methylene propane (60% yield) were obtained as a pale yellow transparent liquid.

The results for the gas chromatographic analysis, elemental analysis, IR absorption spectral analysis and $^1$H NMR analysis were as shown below and it was confirmed that the product has the molecular structure of the following formula:

| | | C | | | | |
|---|---|---|---|---|---|---|
| | | H | | | | |
| a | b | d | e | f | g | |
| CH₂=C(CH₂NCH₂CH₂CH₂CH₃)₂ | | | | | | |

Gas chromatographic analysis: purity 94.9%

IR absorption spectral analysis (liquid film method)

| Number of wave (cm⁻¹) | Belonging to |
|---|---|
| 3250 | N—H |
| 2900~2750 | C—H |
| 1640 | C=C |

¹NMR analysis (90 MHz in CDCl₃)

| Position | Chemical shift δ (ppm) | Integral intensity | Multiplicity |
|---|---|---|---|
| a | 5.0 | 2H | s |
| b | 3.3 | 4H | s |
| c | 1.2 | 2H | s |
| d | 2.4~2.7 | 4H | t |
| e | 1.3~1.7 | 4H | d |
| f | 1.3~1.7 | 4H | m |
| g | 0.8~1.1 | 6H | m |

Mass spectral analysis (m/e) 198 (M⁺)

EXAMPLE 9

Synthesis of 2-(N-(n-butyl)aminomethyl)-3-(N-(n-butyl)amino)propyl trimethoxysilane 198 parts of 2-methylene-1,3-bis(N-(n-butyl)amino)-propane obtained in Reference Example 1 and 0.04 parts (as platinum atom) of a platinum complex containing 1,3,5,7-tetravinyl-1,3,5,7-tetramethylcyclotetrasiloxane as a ligand were charged into a flask of 1 liter inner volume, equipped with a stirrer, a thermometer, a dropping funnel, a refluxing condenser and an oil bath. Stirring was started and the mixture was heated at a liquid temperature of 70° C.

122 parts of trimethoxysilane were dropped onto the solution from the dropping funnel for one hour with heating such that the liquid temperature was kept at 70°~90° C. After dropping was complete, the mixture was heated under stirring for 3 hours at a liquid temperature of 90° C. and it was confirmed form the gas chromatographic analysis that the peak of the starting material was eliminated.

Then, after standing to cool to a room temperature, when fractions boiling at 164°~166° C./2 Torr were collected by distillation under a reduced pressure, 256 parts (80.0% yield) of 2-N-(n-butyl)aminomethyl)-3-N-(n-butyl)amino)-propyl trimethoxysilane were obtained as a colorless transparent liquid.

The results for the gas chromatographic analysis, elemental analysis, IR absorption spectroscopy and ¹H NMR analysis were as shown below and it was confirmed that the product had the molecular structure of the following formula:

| | | | | e | | | | |
|---|---|---|---|---|---|---|---|---|
| | | | | H | | | | |
| a | b | c | d | f | g | h | i | |
| (CH₃O)₃SiCH₂CH(CH₂NCH₂CH₂CH₂CH₃)₂ | | | | | | | | |

Gas chromatographic analysis: purity 95.1%

Elemental analysis:

| Measured value: | Si: 8.80%, C: 56.17%, H: 11.29% O: 15.00% N: 8.74% |
|---|---|
| Calculated value | Si: 8.76%, C: 56.20%, H: 11.32%, O: 14.98% N: 8.74 |

IR absorption spectral analysis (liquid film method)

| Number of wave (cm⁻¹) | Belonging to |
|---|---|
| 3250 | N—H |
| 2900~2750 | C—H |
| 1100~1080 | Si—OCH₃ |

¹NMR analysis (90 MHz in CDCl₃)

| Position | Chemical shift δ (ppm) | Integral intensity | Multiplicity |
|---|---|---|---|
| a | 3.5 | 9H | s |
| b | 0.4~0.6 | 2H | d |
| c | 1.7~2.1 | 1H | m |
| d | 2.5~2.7 | 4H | d |
| e | 1.2~1.3 | 2H | bs |
| f | 2.4~2.7 | 4H | t |
| g | 1.2~1.5 | 4H | m |
| h | 1.2~1.5 | 4H | m |
| i | 0.8~1.0 | 6H | d |

Mass spectral analysis (m/e) 320 (M⁺)

While the invention has been described in detail and with reference to specific embodiments thereof, it will be apparent to one skilled in the art that various changes and modifications can be made therein without departing from the spirit and scope thereof.

What is claimed is:

1. An organosilicon compound represented by the general formula:

$$X_2CHCH_2SiY_n \quad (R^1)_{3-n} \qquad (1)$$

R¹ represents a substituted or non-substituted monovalent hydrocarbon group. X represents ClCH₂—,

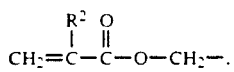

$$CH_2=C-C-O-CH_2- \quad \overset{R^2}{\underset{}{|}} \overset{O}{\underset{}{\|}}$$

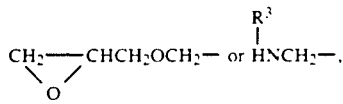

$$CH_2\underset{O}{\overset{}{\diagdown\diagup}}CHCH_2OCH_2- \text{ or } HNCH_2-, \quad \overset{R^3}{\underset{}{|}}$$

Y represents a hydrolyzable group or a hydroxyl group, n represents a number of 1, 2 or 3, R² represents a hydrogen atom or a methyl group and R³ represents a hydrogen atom or a substituted or non-substituted monovalent hydrocarbon group.

2. An organosilicon compound as defined in claim 1, wherein Y is an alkoxy group, hydroxyl group or halogen atom.

3. An Organosilicon compound as defined in claim 1, wherein Y is a methoxy group.

4. An organosilicon compound as defined in claim 1, wherein R¹ is a methyl group.

5. An organosilicon compound as defined in claim 1, wherein R³ is a hydrogen atom or a butyl group.

6. An acrylic compound represented by the general formula:

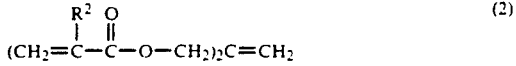

$$(CH_2=C-C-O-CH_2)_2C=CH_2 \quad \overset{R^2}{\underset{}{|}} \overset{O}{\underset{}{\|}} \qquad (2)$$

which R² have the same meanings as defined in claim 1.

* * * * *